(12) United States Patent
Frangioni et al.

(10) Patent No.: US 10,087,153 B2
(45) Date of Patent: Oct. 2, 2018

(54) METHOD OF PREPARING DIAMINOPHENOTHIAZINIUM

(71) Applicant: Curadel, LLC, Marlborough, MA (US)

(72) Inventors: John V. Frangioni, Wayland, MA (US); Paul Caffrey, North Falmouth, MA (US)

(73) Assignee: Curadel, LLC, Marlborough, MA (US)

( * ) Notice: Subject to any disclaimer, the term of this patent is extended or adjusted under 35 U.S.C. 154(b) by 0 days.

(21) Appl. No.: 15/387,017

(22) Filed: Dec. 21, 2016

(65) Prior Publication Data

US 2017/0183320 A1     Jun. 29, 2017

Related U.S. Application Data

(60) Provisional application No. 62/271,507, filed on Dec. 28, 2015.

(51) Int. Cl.
    C07D 279/20        (2006.01)

(52) U.S. Cl.
    CPC ................... C07D 279/20 (2013.01)

(58) Field of Classification Search
    CPC .................................................. C07D 279/20
    See application file for complete search history.

(56) References Cited

U.S. PATENT DOCUMENTS

| 5,220,009 A | 6/1993 | Mazur et al. |
| 8,765,942 B2 | 7/2014 | Feraud et al. |
| 8,815,850 B2 | 8/2014 | Feraud et al. |

FOREIGN PATENT DOCUMENTS

| EP | 0510668 A2 | 10/1992 |
| GB | 2373787 A | 10/2002 |
| WO | 2003/082296 A1 | 10/2003 |
| WO | 2005/054217 A1 | 6/2005 |
| WO | 2006/032879 A2 | 3/2006 |

OTHER PUBLICATIONS

Wagner, et al., Relation between the solubility and association of dyestuffs in binary aqueous systems, Textil-Praxis, 24(5), 310-14, (6), 383-8 (1969).*

Yu L Ed—Kwon Ick Chan et al. "Amorphous Pharmaceutical Solids: Preparation, Characterization and Stabilization", Advanced Drug Delivery Reviews, Elsevier, Amsterdam, NL, vol. 48, No. 1, May 16, 2001, pp. 27-42.

Hancock B C et al. "Characteristics and Significance of the Amorphous State in Pharmaceutical Systems", Journal of Pharmaceutical Sciences, American Pharmaceutical Association, Washington, US, vol. 86, No. 1, Jan. 1, 1997, pp. 1-12.

International Search Report issued in PCT/US2016/068012, dated Feb. 27, 2017.

\* cited by examiner

*Primary Examiner* — Erich A Leeser
(74) *Attorney, Agent, or Firm* — Locke Lord LLP; Nicholas J. DiCeglie, Jr.

(57) ABSTRACT

Disclosed herein are methods for preparing ultrapure diaminophenothiasinium compounds with high solubility in solutions, e.g., water, and the compositions provided therefrom.

18 Claims, 1 Drawing Sheet

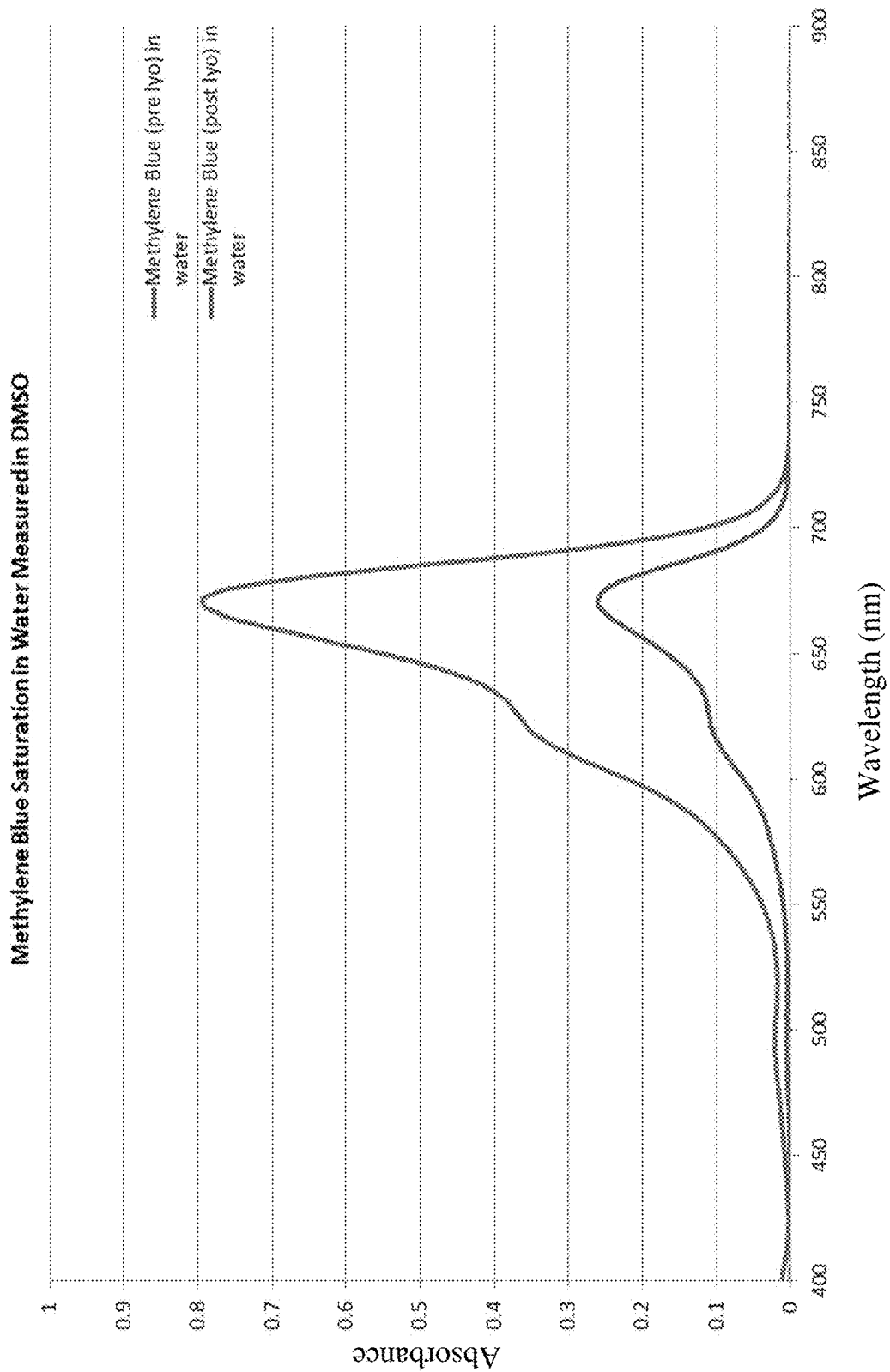

METHOD OF PREPARING DIAMINOPHENOTHIAZINIUM

CROSS REFERENCE TO RELATED APPLICATIONS

This application claims the benefit of priority of U.S. Provisional Patent Application No. 62/271,507, filed Dec. 28, 2015, the contents of which are hereby incorporated by reference herein in its entirety.

STATEMENT REGARDING FEDERALLY SPONSORED RESEARCH OR DEVELOPMENT

This invention was made with Government support under Grant #CA115296, awarded by NIH. The Government has certain rights in the invention.

FIELD OF THE INVENTION

Embodiments of the present disclosure are novel processes for preparing compounds of the diaminophenothiazinium type, in particular a process for lyophilizing these compounds. Additional embodiments of the present disclosure relate to methylene blue, and the products resulting from the process of the present disclosure and the concentration thereof, which is higher than those known in the prior art. The disclosure also relates to the use of these compounds for the preparation of medicaments.

BACKGROUND OF THE INVENTION

Methylene blue, which is also known as methylthioninium chloride or 3,7-bis(dimethylamino)phenothiazin-5-ylium chloride, is an organic compound that corresponds to the formula below:

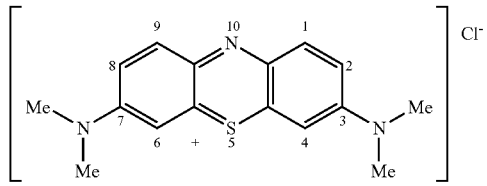

Methylene blue has been used as a redox indicator and dye, an optical developer in biophysical systems, in nanoporous materials as a separating material, and in photoelectrochromic imaging. Methylene blue has also been used as an antiseptic, anti-infective, as an antidote (i.e., a remedy to counteract the effects of a poison) and as a diagnostic agent. Methylene blue has found uses in many medical fields, including gynecology, neonatology, cancerology, oncology, urology, ophthalmology and gastroenterology.

In particular, methylene blue can be used to prevent or inhibit an exaggerated hymodynamic reaction (WO 2003/082296). That is, methylene blue or a related compound can be used to prevent or reverse hypotension, unstable angina, myocardial infarction or shock caused by the concomitant ingestion of a phosphodiesterase inhibitor, such as sildenafil citrate, and a NO-donor, such as L-arginine, or an organic nitrate, such as nitroglycerin.

Methylene blue has also been shown to reduce pathogenic contaminants in the blood (GB2373787). Methylene blue or derivatives thereof may also be used or incorporated in pharmaceutical compositions, medical devices, woven and non-woven fibers, dyestuffs and surface coating materials.

Methods of synthesizing the above compound require metal compounds in at least one synthetic step. For example, patent DE-1886 describes a process with oxidative coupling of N,N-dimethyl-1,4-diaminobenzene carried out with $H_2S$ and $FeCl_3$. Fiez David et al. ("Fundamental Processes of Dye Chemistry", Interscience, pages 308-314 (1949)) describes a process in which the thiazine ring is formed by treatment with manganese dioxide or with copper sulfate, and a treatment with zinc chloride, sodium dichromate and aluminum thiosulfate. WO 2005/054217 describes a method of preparing methylene blue derivatives with phenothiazine as starting product. Methods for preparing phenothiazine require metal reactants in which the metal atoms chelate the phenothiazine at the end of the synthesis. Therefore, methylene blue produced by this process are naturally contaminated with metal residues, as well as the organic contaminants, such as azure B, that are typically present. WO 2006/032879 describes a process for preparing methylene blue that includes three steps comprising metal compounds, for example, (1) a reduction step with iron, (2) an oxidation step with sodium dichromate, and (3) an oxidation step with copper sulfate.

Expensive purification steps are utilized to reduce the impurities, particularly metal impurities, in methylene blue and other diaminophenothiazinium type compounds. Nevertheless, these various processes produce methylene blue with metal and organic impurities. Despite asserting that metal impurities representing 10% of the maximum threshold of the European Pharmacopeia can be achieved, the examples of WO 2006/032879 demonstrates that the process described therein does not achieve this for all metals simultaneously and are not always reproducible. The European Pharmacopeia was amended in April 2006 to provide an increase in the threshold tolerances for metal impurities because methylene blue cannot be effectively produced within the previous requirements, especially at industrial amounts.

U.S. Pat. No. 8,765,942 B2 and U.S. Pat. No. 8,815,850 B2 describe a process of preparing diaminophenothiazinium compounds, for example, methylene blue that has a high degree of purity, both of which are incorporated herein by reference in their entirety. In particular, the publications describe a process which provides a highly pure, e.g., methylene blue with very low levels of metal and organic impurities that can be extrapolated to an industrial scale. However, this process results in low solubility in water of the produced ultrapure methylene blue.

Therefore, there exists a need for ultrapure methylene blue with increased solubility in water, as compared to untreated ultrapure methylene blue, and a process for the production thereof.

SUMMARY OF THE INVENTION

The present description relates to the surprising and unexpected discovery of a process that provides lyophilized ultrapure diaminophenothiasinium compound of Formula (I). In particular, the present disclosure describes a process that quadruples the solubility of diaminophenothiasinium compounds in water. As such, the present disclosure also provides for ultrapure diaminophenothiasinium compounds with a water solubility of about 5 mg/mL to about 30 mg/mL. The ultrapure diaminophenothiasinium compound(s) can be prepared as described in U.S. Pat. No.

8,765,942 B2 and U.S. Pat. No. 8,815,850 B2, which until now only demonstrated a solubility in water of about 5 mg/mL.

A first object of the present disclosure is a method of preparing an ultrapure diaminophenothiasinium compound. The method comprises lyophilizing at least one diaminophenothiasinium compound from a solvent solution. The method can further comprise, prior to the lyophilizing: adding at least one diaminophenothiasinium compound to a water-MeOH mixture with a water to MeOH ratio in a range of about a 3:1 to about 1:3 (e.g., 1:1); passing the diaminophenothiasinium compound solution through a gradient with mobile phases of about 5 mM to about 20 mM HCl in water (e.g., 12 mM) and about 4 mM to about 20 mM HCl in MeOH (e.g., 12 mM); collecting fractions; concentrating the diaminophenothiasinium compound containing fraction (e.g., by vacuum); dissolving the concentrated diaminophenothiasinium compound fraction in solvent; performing centrifugation on the concentrated diaminophenothiasinium compound(s) solvent solution; and filtering the centrifuged diaminophenothiasinium compound(s).

In an embodiment, the at least one compound is of the Formula (I) and/or its equivalent resonant structures (as described below):

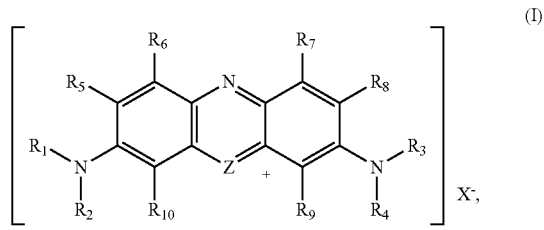

(I)

wherein each of $R_1$, $R_2$, $R_3$, $R_4$, $R_5$, $R_6$, $R_7$, $R_8$, $R_9$ and $R_{10}$ may be chosen, independently of the others, from the group constituted of: a hydrogen atom; saturated or unsaturated, linear, branched or cyclic $C_1$-$C_6$ alkyl groups, optionally substituted with one or more functions chosen from a halogen atom, and a $C_1$-$C_6$ alkoxy, $C_1$-$C_6$ alkyloxycarbonyl or —$CONH_2$ function, aryl groups optionally substituted with one or more functions chosen from: a $C_1$-$C_4$ alkyl, a halogen atom, and a $C_1$-$C_6$ alkoxy, $C_1$-$C_6$ alkyloxycarbonyl or —$CONH_2$ function. In a particular embodiment, $R_6$ and $R_7$ may be chosen from methyl, ethyl, or —OH. Two successive $R_i$ groups (i=1, 2 . . . 10) of Formula (I) may be joined to form a ring. For example, $R_1$ with $R_5$, or $R_5$ with $R_6$, $R_7$ with $R_8$, $R_8$ with $R_3$, $R_3$ with $R_4$, $R_4$ with $R_9$, $R_{10}$ with $R_2$, or $R_2$ with $R_1$ may consist of a single alkyl chain that is optionally substituted forming a fourth ring. Each of $R_5$-$R_{10}$ can be chosen, independently of the others, from the halogen atoms: F, Cl, Br and I. Z is an atom selected from O or S. $X^-$ represents an organic or inorganic anion, which can include: the anions of inorganic acids such as, for example, hydrochloric acid, hydrobromic acid, sulfuric acid, phosphoric acid or nitric acid; the anions of organic acids such as, for example, acetic acid, trifluoroacetic acid, oxalic acid, tartaric acid, succinic acid, maleic acid, fumaric acid, gluconic acid, citric acid, malic acid, ascorbic acid and/or benzoic acid; and $OH^-$.

In an embodiment, a saturated diaminophenothiasinium solution in water is made with a concentration≥about 10 mg/mL.

In an embodiment, the method further comprises producing a saturated DMSO solution with the ultrapure diaminophenothiasinium compound with high solubility. The DMSO saturated solution can have a concentration of diaminophenothiasinium in a range of about 15 mg/mL to about 25 mg/mL (e.g., about 20 mg/mL).

In an embodiment, filtering the centrifuged diaminophenothiasinium compound(s) is performed with a filter comprising pores in a range of about 0.22 μm to about 0.8 μm (e.g., about 0.45 μm). Any filter that one skilled in art would appreciate to be appropriate may be utilized. For example, the filter is a Teflon filter or a nylon filter. In a particular embodiment, the filter is a 0.45 μm Teflon filter. Filtering the centrifuged diaminopheothiasinium compound(s) removes undissolved solids from the solution.

A second object of the present disclosure is a composition comprising at least one diaminophenothiasinium compound of Formula (I) (which may include its resonant structures) with increased solubility in water. In an embodiment, the diaminophenothiasinium compound has a solubility in water in a range of about 5 mg/ml to about 30 mg/mL (e.g., about 15 mg/mL to about 20 mg/mL).

The preceding general areas of utility are given by way of example only and are not intended to be limiting on the scope of the present disclosure and appended claims. Additional objects and advantages of the present invention will be appreciated by one of ordinary skill in the art in light of the instant claims, description, and examples. For example, the various aspects and embodiments of the invention may be utilized in numerous combinations, all of which are expressly contemplated by the present description. These additional objects and advantages are expressly included within the scope of the present invention.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention.

FIG. 1. Illustrates absorbance measurements for saturated solutions of compounds prior to lyophilization and post lyophilizations in accordance with embodiments of the invention.

DETAILED DESCRIPTION

The following is a detailed description of the disclosure provided to aid those skilled in the art in practicing the present disclosure. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description of the disclosure herein is for describing particular embodiments only and is not intended to be limiting of the disclosure. All publications, patent applications, patents, figures and other references mentioned herein are expressly incorporated by reference in their entirety.

As described herein, the process of the present disclosure provides lyophilized ultrapure diaminophenothiasinium compound of Formula (I) with markedly higher solubility in water than previous ultrapure diaminophenothiasinium compounds. In particular, the present disclosure describes a process that quadruples the solubility of diaminophenothiasinium compounds in water. As such, the present disclosure also provides for ultrapure diaminophenothiasinium compounds with a solubility in water in a range of about 5 mg/mL to about 30 mg/mL. The ultrapure diaminophenothiasinium compound(s) utilized in the process can be prepared as described in U.S. Pat. No. 8,765,942 B2 and U.S. Pat. No. 8,815,850 B2, which until now only demonstrated a solubility in water of about 5 mg/mL.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the 10 United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

In embodiments of the present disclosure, a process for the production of lyophilized ultrapure diaminophenothiasinium compound of Formula (I) is provided. In particular, the present disclosure describes a process that quadruples the solubility of diaminophenothiasinium compounds in water. As such, the present disclosure also provides for ultrapure diaminophenothiasinium compounds with a water solubility of about 5 mg/mL to about 30 mg/mL.

A first object of the present disclosure is a method of preparing an ultrapure diaminophenothiasinium compound. The method comprises lyophilizing at least one diaminophenothiasinium compound from a DMSO solution. The method can further comprise, prior to the lyophilizing: adding at least one diaminophenothiasinium compound to a water-MeOH mixture with a water to MeOH ratio in a range of about a 3:1 to about 1:3 (e.g., 1:1); passing the diaminophenothiasinium compound solution through a gradient with mobile phases of about 5 mM to about 20 mM HCl in water (e.g., 12 mM) and about 4 mM to about 20 mM HCl in MeOH (e.g., 12 mM); collecting fractions; concentrating the diaminophenothiasinium compound containing fraction; dissolving the concentrated diaminophenothiasinium compound fraction in a solvent; performing centrifugation on the concentrated diaminophenothiasinium compound(s) solvent solution; and filtering the centrifuged diaminophenothiasinium compound(s). The ultrapure diaminophenothiasinium compound(s) can be prepared as described in U.S. Pat. No. 8,765,942 B2 and U.S. Pat. No. 8,815,850 B2, which without the presently described process only demonstrate a solubility in water of about 5 mg/mL.

Collecting fractions can comprise selecting fractions having no Azure B impurity. Selection of the fraction can be accomplished with liquid chromatography-mass spectroscopy (LC-MS). The concenrting can be performed by, e.g., vacuum or rotary evaporation. If rotary evaporation is utilized the temperature is less than or equal to 50° C. Centrifugation can be performed at 3,500 RPM (e.g., about 2,600 RCF to about 3,000 RCF) for 10 minutes in, e.g., polypropylene tubes. In a particular embodiment, the centrifugation is performed in a range of about 2,700 RCF to about 2,900 RCF (e.g., about 2,800 RCF).

In a particular embodiment, the solvent comprises DMSO. In another embodiment, the solvent further comprises at least one co-solvent (e.g., 1, 2, 3, 4, 5, 6, 7, 8, 9, or 10 co-solvents). The co-solvent can comprise: acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroetane, diethylene glycol, diethyl ether, diglyme, 1,2-dimethoxy-ethane, dimethylformamide, 1,4-dioxane, ethanol ethyl acetate, ethylene glycol, glycerin, heptane, hemamethylphophoramie, hexamethylphosphorous triamide, hexane, methanol, methyl t-butyl ether, methylene chloride, N-methyle-2-pyrrolidinone, nitromethane, pentane, petroleum ether, 1-propanol, 2-propanol, pyridine, tetrahydrofuran, toluene, triethyl amine, o-xylene, m-xylene, p-xylene, or any combination thereof.

The solvent can further comprise a lyophilization excipient. Excipients are well known in the art of lyophilization. In another embodiment, the lyophilization excipient includes at least one of: a buling agent, a buffering agent, or a solubilizing agent. For example, the excipient may comprise at least one bulking agent selected from the group consisting of acetic acid, detran, glucose, glycine, hexose, histidine, lactose, L-arginine, mannitol, polyethylene glycol, PVP (K40), raffinose, sorbitol, sucrose, and trehalose. The excipient can comprise at least one buffering agent selected from citric acid, sodium citrate, potassium citrate, tartaric acid, sodium phosphate, tris base, tris HCl, tris acetate, zinc chloride, sodium acetate, potassium acetate, arginine, hydrochloric acid, sodium hydroxide, and meglumine. The excipient can comprise at least one solubilizing agent selected from the group consisting of ethylenediamine tetra acetic acid (EDTA), alpha cyclodextrin, hydroxypropyl-β-cyclodextrin, polysorbate 80, tert-butyl alcohol, iso-propyl alcohol, dichloromethane, ethanol, acetone, and glycerol.

The solvent can comprise at least 90% DMSO. In an embodiment, the solvent comprises DMSO in a range of about 50% to about 100% of the solvent, about 60% to about 100% of the solvent, about 70% to about 100% of the solvent, about 80% to about 100% of the solvent, about 90% to about 100% of the solvent, about 50% to about 90% of the solvent, about 60% to about 90% of the solvent, about 70% to about 90% of the solvent, about 80% to about 90% of the solvent, about 50% to about 80% of the solvent, about 60% to about 80% of the solvent, about 70% to about 80% of the solvent, about 50% to about 70% of the solvent, or about 60% to about 70% of the solvent. comprise at least about 50% DMSO, about 55% DMSO, about 60% DMSO, about 65% DMSO, about 70% DMSO, about 75% DMSO, about 80% DMSO, about 85% DMSO, about 90% DMSO, about 95% DMSO, or about 100% DMSO.

In an embodiment, the at least one compound is of the Formula (I) and/or its equivalent resonant structures (as described below):

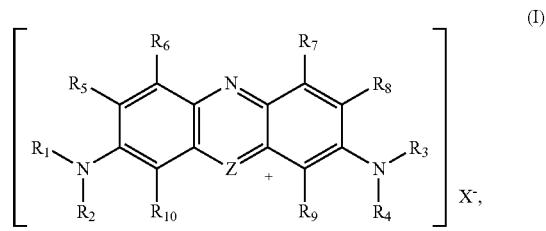

wherein each of $R_1$, $R_2$, $R_3$, $R_4$, $R_5$, $R_6$, $R_7$, $R_8$, $R_9$ and $R_{10}$ may be chosen, independently of the others, from the group constituted of: a hydrogen atom; saturated or unsaturated, linear, branched or cyclic $C_1$-$C_6$ alkyl groups, optionally substituted with one or more functions chosen from a halogen atom, and a $C_1$-$C_6$ alkoxy, $C_1$-$C_6$ alkyloxycarbonyl or —$CONH_2$ function, aryl groups optionally substituted with one or more functions chosen from: a $C_1$-$C_4$ alkyl, a halogen atom, and a $C_1$-$C_6$ alkoxy, $C_1$-$C_6$ alkyloxycarbonyl or —$CONH_2$ function. Two successive $R_i$ groups (i=1, 2 ... 10) of Formula (I) may be joined to form a ring. For example, $R_1$ with $R_5$, or $R_5$ with $R_6$, $R_7$ with $R_8$, $R_8$ with $R_3$, $R_3$ with $R_4$, $R_4$ with $R_9$, $R_{10}$ with $R_2$, or $R_2$ with $R_1$ may consist of a single alkyl chain that is optionally substituted forming a fourth ring. $R_6$, $R_7$ can be chosen from methyl, ethyl, or —OH. Each of $R_5$-$R_{10}$ can be chosen, independently of the others, from the halogen atoms: F, Cl, Br and I. Z is an atom selected from O or S. $X^-$ represents an organic or inorganic anion, which can include: the anions of inorganic acids such as, for example, hydrochloric acid, hydrobromic acid, sulfuric acid, phosphoric acid or nitric acid; the anions of organic acids such as, for example, acetic acid, trifluoroacetic acid, oxalic acid, tartaric acid, succinic acid, maleic acid, fumaric acid, gluconic acid, citric acid, malic acid, ascorbic acid and/or benzoic acid; and $OH^-$.

In an additional embodiment, the method further comprises making a saturated solvent solution with the at least one diaminophenothiasinium compound. In certain embodiments, the concentration of at the at least one diaminophenothiasinium compound in the saturated solvent solution is in a range of about 15 mg/mL to about 25 mg/mL (e.g., about 18 mg/mL to about 22 mg/mL or about 20 mg/mL). The saturated solvent solution can be utilized to make a diaminophenothiasinium compound solution in water. The diaminophenothiasinium compound solution in water can have a concentration of diaminothiasinium compound(s) greater than or equal to about 10 mg/mL.

In an embodiment, a saturated diaminophenothiasinium solution in water is made with a concentration greater than or equal to about 10 mg/mL. In particular embodiments, the saturated solution in water has a concentration of diaminophenothiasinium in a range of about 10 mg/mL to about 30 mg/mL, about 10 mg/mL to about 27.5 mg/mL, about 10 mg/mL to about 25 mg/mL, about 10 mg/mL to about 22.5 mg/mL, about 10 mg/mL to about 20 mg/mL, about 10 mg/mL to about 17.5 mg/mL, about 10 mg/mL to about 15 mg/mL, about 10 mg/mL to about 12.5 mg/mL, 12.5 mg/mL to about 30 mg/mL, about 12.5 mg/mL to about 27.5 mg/mL, about 12.5 mg/mL to about 25 mg/mL, about 12.5 mg/mL to about 22.5 mg/mL, about 12.5 mg/mL to about 20 mg/mL, about 12.5 mg/mL to about 17.5 mg/mL, about 12.5 mg/mL to about 15 mg/mL, 15 mg/mL to about 30 mg/mL, about 15 mg/mL to about 27.5 mg/mL, about 15 mg/mL to about 25 mg/mL, about 15 mg/mL to about 22.5 mg/mL, about 15 mg/mL to about 20 mg/mL, about 15 mg/mL to about 17.5 mg/mL, 17.5 mg/mL to about 30 mg/mL, about 17.5 mg/mL to about 27.5 mg/mL, about 17.5 mg/mL to about 25 mg/mL, about 17.5 mg/mL to about 22.5 mg/mL, about 17.5 mg/mL to about 20 mg/mL, 20 mg/mL to about 30 mg/mL, about 20 mg/mL to about 27.5 mg/mL, about 20 mg/mL to about 25 mg/mL, about 20 mg/mL to about 22.5 mg/mL, 22.5 mg/mL to about 30 mg/mL, about 22.5 mg/mL to about 27.5 mg/mL, about 22.5 mg/mL to about 25 mg/mL, 25 mg/mL to about 30 mg/mL, about 25 mg/mL to about 27.5 mg/mL, or about 27.5 mg/mL to about 30 mg/mL. In certain embodiments, the saturated diaminophenothiasinium solution in water has a concentration of about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL.

In an embodiment, the concentrated diaminophenothiasinium compound solvent solution is a saturated solution. For example, the concentrated diaminophenothiasinium compound solvent solution is in a range of about 15 mg/mL to about 25 mg/mL (e.g., about 18 mg/mL to about 22 mg/mL or about 20 mg/mL.

In an embodiment, filtering the centrifuged diaminophenothiasinium compound(s) is performed with a filter comprising pores in a range of about 0.22 μm to about 0.8 μm (e.g., about 0.45 μm). Any filter that one skilled in art would appreciate to be appropriate may be utilized. For example, the filter is a Teflon filter or a nylon filter. In a particular embodiment, the filter is a 0.45 μm Teflon filter. Filtering the centrifuged diaminopheothiasinium compound(s) removes undissolved solids from the solution.

A second object of the present disclosure is a composition comprising at least one diaminophenothiasinium compound of Formula (I) (which may include its resonant structures) with increased solubility in water. In an embodiment, the diaminophenothiasinium compound has a solubility in water in a range of about 5 mg/ml to about 30 mg/mL (e.g., about 15 mg/mL to about 20 mg/mL).

In an embodiment, the diaminophenothiasinium compound of Formula (I) and/or its equivalent resonant structures is/are prepared by the process described in U.S. Pat. No. 8,765,942 B2 and U.S. Pat. No. 8,815,850 B2. That is, the process includes at least one step during which a compound of formula (II):

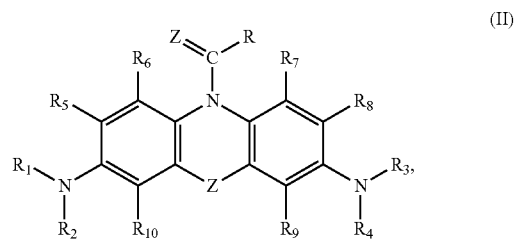

is subjected to a purification step under conditions which make it possible to separate metal compounds from the compounds of formula (II), the $R_1$, $R_2$, $R_3$, $R_4$, $R_5$, $R_6$, $R_7$, $R_8$, $R_9$ and $R_{10}$ groups having the same definition as in Formula (I), and R representing a group chosen from: a phenyl or benzyl group, optionally substituted with one or more functions chosen from: a $C_1$-$C_4$ alkyl, a halogen atom, a $C_1$-$C_4$ haloalkyl and a nitro group; a linear, branched or cyclic $C_1$-$C_8$ alkyl group; a $C_1$-$C_8$ alkylamino group; a $C_1$-$C_8$ alkoxy group; and a phenyloxy or benzyloxy group optionally substituted on the aromatic nucleus with one or more functions chosen from: a $C_1$-$C_4$ alkyl, a halogen atom, a $C_1$-$C_4$ haloalkyl and a nitro group. Z are atoms independently selected from O and S.

The purification of the compounds of formula (II) is performed under conditions that make separate metal compounds from the compounds of formula (II), for example, filtration through a support that retains the metal compounds, crystallization from an appropriate solvent, or any other method known to those skilled in the art.

When the purification is carried out by filtration through a support capable of retaining the metal compounds, such a support may be chosen from: a silica gel, an alumina gel (neutral, basic or acidic), an optionally modified diatomite, celite, a microporous membrane, resins grafted with metal-capturing groups and fibers grafted with metal-capturing groups, such as thiol, carboxylic acid or tertiary amine functions, or any other support having the property of retaining metals.

The compound of Formula (II) can be obtained from the compound of formula (I), by reduction of the compound of formula (I) and then by reaction of the amine function of the phenothiazinium ring with a suitable protective group R—CZ—Y in which R and Z have the same definition as above and Y represents a leaving group chosen from: a halogen atom such as F, Cl, I or Br; a $C_1$-$C_6$ alkoxy group; a —OCOR (anhydride) group, and a hydroxyl group, optionally in the presence of an activator of the dicyclohexylcarbodiimide (DCC) type. R is chosen from a phenyl group and a toluoyl group.

When the compound of formula (II) is obtained starting from the compound of formula (I), the overall process is a purification of the compound of formula (I). The compound of formula (II) can be obtained by other processes that do not use the compound of Formula (I) as a starting product.

As mentioned above, the compound represented by formula (I) includes equivalent resonant structures, for example, those shown below as Formulas (IA), (IB), and (IC):

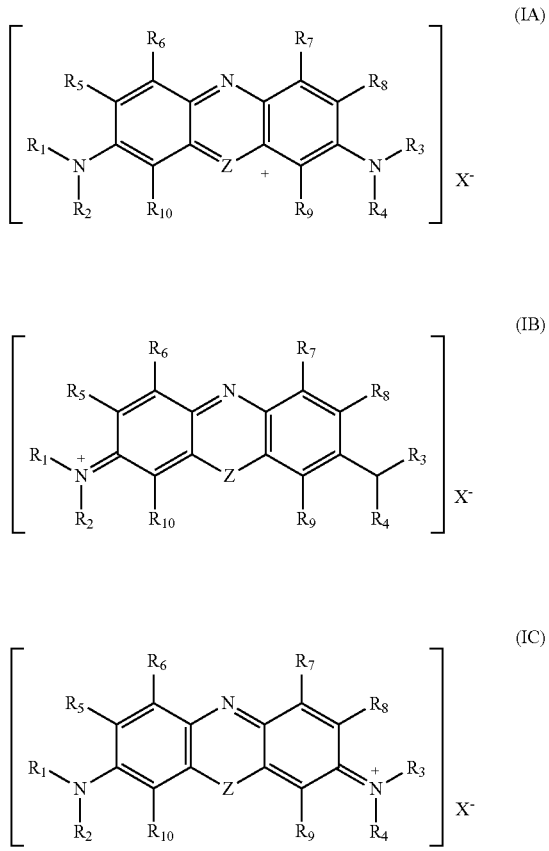

wherein $R_1$, $R_2$, $R_3$, $R_4$, $R_5$, $R_6$, $R_7$, $R_8$, $R_9$ and $R_{10}$, defined the same as with Formula (I), and each independently selected. In an embodiment, $R_1$-$R_{10}$ are chosen from a hydrogen atom and a $C_1$-$C_4$ alkyl. In a particular embodiment, $R_5$, $R_8$, $R_9$ and $R_{10}$ are H.

In certain embodiments, at least one of the following conditions are met: X represents Cl or OH; $R_1$, $R_2$, $R_3$ and $R_4$ are independently selected from a hydrogen atom and methyl; $R_6$ is a hydrogen atom; $R_7$ is a hydrogen atom; and Z is O. In another embodiment, the compound of formula (I) is tetramethylthionine chloride or methylene blue. In an embodiment, the compound of formula (I) is dimethylthionine chloride (i.e. Azure A), or trimethylthionine chloride (i.e., Azure B), or monomethylthionine chloride (i.e., Azure C).

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "aryl," by itself or as part of another substituent means a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present invention at any available stable position on the ring(s) or as otherwise indicated in the chemical structure presented.

As used herein, the term "alkoxy," by itself or as part of another substituent means, is an alkyl group having the designated number of carbon atoms, as defined above, connected to the rest of the molecule via an oxygen.

Additional objects and advantages of the present invention will be appreciated by one of ordinary skill in the art in light of the current description and examples of the preferred embodiments, and are expressly included within the scope of the present invention.

EXAMPLES

Methylene blue powder prepared in accordance with U.S. Pat. Nos. 8,765,942 B2 and 8,815,850 B2. The methylene blue powder was dissolved in 1:1 water MeOH (saturated solution has a solubility of about 26 mg, measured in DMSO using the previously determined molar extinction of 100,500). The solution was passed through a gradient containing mobile phases of 12 mM HCl in water and 12 mM HCl in MeOH. HCl is used to avoid any possibility of replacing the counter ion of methylene blue, which is recognized as Cl. Pure fractions were collected and concentrated en vacuo, obtaining a dry, flaky dark blue solid methylene blue.

The saturation of the concentrated methylene blue in water and DMSO was examined. For example, the saturation for each of the following conditions are shown: (1) DMSO: 21 mg/mL; (2) 10% DMSO in water: 3.2 mg/mL; (3) 10% water in DMSO: 16.2 mg/mL; and (4) water: 8.4 mg/mL.

The concentrated methylene blue was dissolved as a saturated solution in DMSO and centrifuged. The centrifuged methylene blue was then filtered through 0.45 μm Teflon filter to remove undissolved solids and lyophilize the ultrapure methylene blue, thereby producing an ultrapure methylene blue with increased solubility in water. For example, DMSO for lyophilization conducted was performed on 10 mg of concentrated methylene blue at 10.5 mg overfill aim—0.59 mL.

Post lyophilization solubility was examined as follows: adding 100 μL of solvent to a vial with 10 mg of lyophilized methylene blue; vortexing the mixture; soliciting the mixture for 30 seconds, filtering the solution through a 0.45 μm nylon spin filter; and measuring absorbance. Absorbance at 670 nm allows for a determination regarding the level/concentration of lyophilized methylene blue, while absorbance at 210 nm and 660 nm allows for a purity determination of the lyophilized methylene blue. Lyophilized methylene blue demonstrated the following solubilities under each of the specified conditions: DMSO: 19.6 mg/mL; PBS-0.1% tween: 1.8 mg/mL; FBS-100 mM HEPES: 13.9 mg/mL; DI water: 45 mg/mL. The molar extinction was 91,000 for FMS, in contrast to the DMSO which has a molar extinction of 100,500. The lyophilized ultrapure methylene blue was greater than 95% pure.

Furthermore, FIG. 1 illustrates the solubility of unlyophilized (that is pre-lyophilization) ultrapure methylene blue in water and the solubility of lyophilized ultrapure methylene blue in water. As can be seen, the method described herein demonstrates a surprising and unexpected increase in the solubility of ultrapure methylene blue in water. The absorbance and the calculations performed therefrom are shown in Table 1 below.

TABLE 1

Summary of Methylene Blue Saturation in Water
Measured in DMSO Pre- and Post-Lyophilization.

| | Methylene Blue | |
|---|---|---|
| | Pre-Lyophilization | Post Lyophilization |
| Sample Solvent | Water | Water |
| Measurement Solvent | DMSO | DMSO |
| Wavelength (nm) | 671.0476685 | 671.0476685 |
| Blank (AU) | 0.00363402 | 0.000288673 |
| Sample (AU) | 0.257421017 | 0.798121095 |
| Molar Ex Coeff. | 100500 | 100500 |
| Sample Concentration (uM) | 2.561403151 | 7.941503433 |
| Dilution Factor | 10000 | 10000 |
| Saturation Concentration (mM) | 25.61403151 | 79.41503433 |
| Mol. Weight (g/mol) | 319.85 | 319.85 |
| Saturation (mg/mL) | 8.192647979 | 25.40089873 |

As would be understood by those of skill in the art, certain quantities, amounts, and measurements are subject to theoretical and/or practical limitations in precision, which are inherent to some of the instruments and/or methods. Therefore, unless otherwise indicated, it is contemplated that claimed amounts encompass a reasonable amount of variation.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims.

What is claimed is:

1. A method of preparing an ultrapure diaminophenothiasinium compound with increased solubility in water, the method comprising lyophilizing at least one diaminophenothiasinimum compound from a solvent solution.

2. The method of claim 1, further comprising, prior to lyophilization:
   adding the at least one diaminophenothiasinium compound to a water-MeOH mixture with a water to MeOH ratio in a range of about a 3:1 to about 1:3;
   passing the diaminophenothiasinium compound solution through a gradient with mobile phases of about 5 mM to about 20 mM HCl in water (e.g., 12 mM) and about 4 mM to about 20 mM HCl in MeOH (e.g., 12 mM);
   collecting fractions;
   concentrating the diaminophenothiasinium compound containing fraction;
   dissolving the concentrated diaminophenothiasinium compound fraction in the solvent;
   performing centrifugation on the concentrated diaminophenothiasinium compound(s) solvent solution; and
   filtering the centrifuged diaminophenothiasinium compound(s) to prepare a ultrapure diaminophenothiasinium compound with high solubility.

3. The method of claim 1, wherein the at least one compound is of the Formula (I) and/or its equivalent resonant structures (as described below):

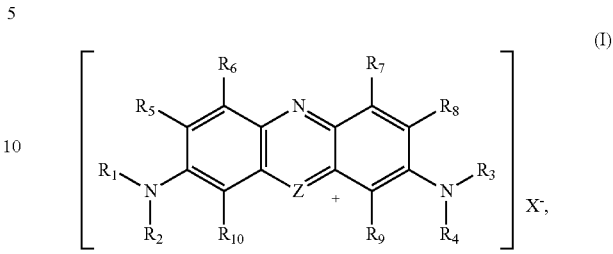

wherein:
   each of $R_1$, $R_2$, $R_3$, $R_4$, $R_5$, $R_6$, $R_7$, $R_8$, $R_9$ and $R_{10}$ is independently selected from the group consisting of: a hydrogen atom ; saturated or unsaturated, linear, branched or cyclic $C_1$-$C_6$ alkyl groups, optionally substituted with one or more functions chosen from a halogen atom, and a $C_1$-$C_6$ alkoxy, $C_1$-$C_6$ alkyloxycarbonyl or —$CONH_2$ function, aryl groups optionally substituted with one or more functions chosen from: a $C_1$-$C_4$ alkyl, a halogen atom, and a $C_1$-$C_6$ alkoxy, $C_1$-$C_6$ alkyloxycarbonyl or —$CONH_2$ function;
   $R_6$ and $R_7$ can be independently selected from methyl, ethyl, or —OH;
   $R_5$-$R_{10}$ can be independently selected from the halogen atoms: F, Cl, Br and I;
   Z is an atom selected from O or S; and
   $X^-$ represents an organic or inorganic anion.

4. The method of claim 3, wherein $X^-$ is selected from: anions of inorganic acids; anions of organic acids; and $OH^-$.

5. The method of claim 2, further comprising producing a saturated DMSO solution with the ultrapure diaminophenothiasinium compound with high solubility.

6. The method of claim 5, wherein the saturated DMSO solution of ultrapure diaminophenothiasinium compound with high solubility has a concentration in a range of about 18 mg/mL to about 22 mg/mL.

7. The method of claim 1, wherein the ultrapure diaminophenothiasinium compound with high solubility is capable of producing a solution in water with a concentration greater than or equal to about 10 mg/mL.

8. The method of claim 2, wherein filtering the centrifuged diaminophenothiasinium compound(s) is performed with a filter with pores in a range of about 0.22 μm to about 0.8 μm.

9. The method of claim 8, wherein the pores are about 0.45 μm.

10. The method of claim 1, wherein the solvent comprises DMSO.

11. The method of claim 10, wherein the solvent further comprise a co-solvent.

12. The method of claim 11, wherein the co-solvent is selected from acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroetane, diethylene glycol, diethyl ether, diglyme, 1,2-dimethoxy-ethane, dimethyl-formamide, 1,4-dioxane, ethanol ethyl acetate, ethylene glycol, glycerin, heptane, hemamethylphophoramie, hexamethylphosphorous triamide, hexane, methanol, methyl t-butyl ether, methylene chloride, N-methyle-2-pyrrolidinone, nitromethane, pentane, petroleum ether, 1-propanol, 2-propanol, pyridine, tetrahydrofuran, toluene, triethyl amine, o-xylene, m-xylene, p-xylene, or any combination thereof.

13. The method of claim 10, wherein the solvent further comprises a lyophilization excipient.

14. The method of claim 13, wherein the lyophilization excipient includes at least one of acetic acid, detran, glucose, glycine, hexose, histidine, lactose, L-arginine, mannitol, polyethylene glycol, PVP (K40), raffinose, sorbitol, sucrose, and trehalose.

15. A composition comprising: at least one diaminophenothiasinium compound with a solubility in water of greater than or equal to about 10 mg/mL.

16. The composition of claim 15, wherein the at least one diaminophenothiasinium compound has a Formula (I):

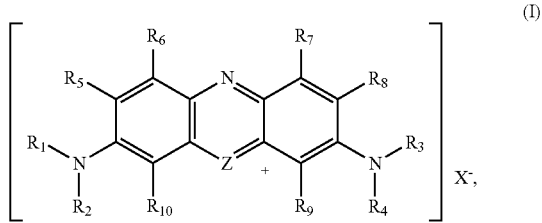

wherein:
each of $R_1$, $R_2$, $R_3$, $R_4$, $R_5$, $R_6$, $R_7$, $R_8$, $R_9$ and $R_{10}$ is independently selected from the group consisting of: a hydrogen atom; saturated or unsaturated, linear, branched or cyclic $C_1$-$C_6$ alkyl groups, optionally substituted with one or more functions chosen from a halogen atom, and a $C_1$-$C_6$ alkoxy, $C_1$-$C_6$ alkyloxycarbonyl or —$CONH_2$ function, aryl groups optionally substituted with one or more functions chosen from: a $C_1$-$C_4$ alkyl, a halogen atom, and a $C_1$-$C_6$ alkoxy, $C_1$-$C_6$ alkyloxycarbonyl or —$CONH_2$ function;

$R_6$ and $R_7$ can be independently selected from methyl, ethyl, or —OH;

$R_5$-$R_{10}$ can be independently selected from the halogen atoms: F, Cl, Br and I;

Z is an atom selected from O or S; and $X^-$ represents an organic or inorganic anion.

17. The composition of claim 16, wherein $X^-$ is selected from: anions of inorganic acids; anions of organic acids; and $OH^-$.

18. A method of preparing an ultrapure diaminophenothiasinium compound with increased solutility in water, the method comprising:
adding the at least one diaminophenothiasinium compound to a water-MeOH mixture with a water to MeOH ratio in a range of about a 3:1 to about 1:3;
passing the diaminophenothiasinium compound solution through a gradient with mobile phases of about 5 mM to about 20 mM HCl in water (e.g., 12 mM) and about 4 mM to about 20 mM HCl in MeOH (e.g., 12 mM);
collecting fractions;
concentrating the diaminophenothiasinium compound containing fraction;
dissolving the concentrated diaminophenothiasinium compound fraction in the solvent;
performing centrifugation on the concentrated diaminophenothiasinium compound(s) solvent solution;
filtering the centrifuged diaminophenothiasinium compound(s) to prepare a ultrapure diaminopheno thiasinium compound with high solubility; and
lyophilizing at least one diaminophenothiasinimum compound from a solvent solution.

* * * * *

UNITED STATES PATENT AND TRADEMARK OFFICE
CERTIFICATE OF CORRECTION

PATENT NO. : 10,087,153 B2
APPLICATION NO. : 15/387017
DATED : October 2, 2018
INVENTOR(S) : Frangioni et al.

It is certified that error appears in the above-identified patent and that said Letters Patent is hereby corrected as shown below:

In the Specification

Column 1, Line 16 the text "Grant # CA115296, awarded by NIH" should read --grant number CA115296, awarded by the National Institutes of Health--

Signed and Sealed this
Tenth Day of February, 2026

John A. Squires
*Director of the United States Patent and Trademark Office*